US006596779B1

(12) United States Patent
Jean-Noel et al.

(10) Patent No.: US 6,596,779 B1
(45) Date of Patent: Jul. 22, 2003

(54) STABLE EMULSION, PROCESS FOR THE PREPARATION THEREOF AND AGENT FOR THIS PURPOSE

(75) Inventors: Bertmo Jean-Noel, Pomacle (FR); Mathaly Philippe, Reims (FR); Régis de Baynast, Versailles (FR); Dubois Véronique, Cosne sur Loire (FR)

(73) Assignee: Agro Industrie Recherches et Developpements, Pomacle (FR)

( * ) Notice: Subject to any disclaimer, the term of this patent is extended or adjusted under 35 U.S.C. 154(b) by 0 days.

(21) Appl. No.: 09/499,870

(22) Filed: Feb. 7, 2000

(30) Foreign Application Priority Data

Feb. 10, 1999 (FR) .............................. 99 01553

(51) Int. Cl.⁷ .......................... B01F 17/56; A01N 25/04
(52) U.S. Cl. ...................... 516/72; 424/70.19; 504/363; 510/417; 514/846; 514/859; 514/943; 514/975; 516/22; 516/28; 516/105
(58) Field of Search ................ 516/22, 28, 72, 516/105; 510/417; 424/70.19; 514/943, 859, 975; 504/363; 536/18.6

(56) References Cited

U.S. PATENT DOCUMENTS

| | | | | |
|---|---|---|---|---|
| H224 H | * | 3/1987 | Malik et al. ............ | 504/363 X |
| 5,133,897 A | * | 7/1992 | Balzer .................... | 516/72 |
| 5,258,358 A | * | 11/1993 | Kocur et al. ............ | 504/363 X |
| 5,466,746 A | * | 11/1995 | Geck et al. .............. | 516/72 X |
| 5,670,471 A | * | 9/1997 | Amalric et al. ......... | 510/417 X |
| 5,688,930 A | * | 11/1997 | Bertho et al. ........... | 536/18.6 |
| 5,795,978 A | * | 8/1998 | Ansmann et al. ....... | 510/417 X |
| 5,888,482 A | * | 3/1999 | Amalric et al. ......... | 516/72 X |
| 6,056,947 A | * | 5/2000 | Kahre et al. ............ | 424/70.19 X |
| 6,087,403 A | * | 7/2000 | Bertho et al. ........... | 516/72 |

FOREIGN PATENT DOCUMENTS

| | | |
|---|---|---|
| EP | 0 628 305 | 12/1994 |
| EP | 0 629 396 | 12/1994 |
| EP | 0 895 805 | 2/1999 |

* cited by examiner

*Primary Examiner*—Richard D. Lovering
(74) *Attorney, Agent, or Firm*—Knobbe, Martens, Olson & Bear, LLP

(57) ABSTRACT

The present invention relates to emulsions which remain perfectly stable over time, prepared from an emulsifier comprising at least one polyglycoside, i.e. polypentoside with or without pohexoside, in which the aliphatic radical has 16 to 18 carbon atoms, and at least one fatty alcohol having 12 to 22 carbon atoms; a process for stabilizing the emulsions; and an emulsifying agent.

18 Claims, No Drawings

STABLE EMULSION, PROCESS FOR THE PREPARATION THEREOF AND AGENT FOR THIS PURPOSE

The present invention relates to emulsions which remain perfectly stable over time, prepared from an emulsifier comprising at least one polyglycoside and at least one fatty alcohol, a process for stabilising the emulsions and an emulsifying agent.

Emulsions are mainly produced and used in industry as substances for consumption or for application to surfaces as carriers for water-insoluble agents. Emulsions are found in cosmetics (lotions, creams, ointments), in cooking (sauces, creams), in pharmaceuticals (ointments, creams), in paint (odour-free paint), in the road industry (emulsified tar), in agrochemicals (phytosanitary products), in detergents, in lamination, iron and steel making and in the production of various deposits (printing, adhesives, etc.).

In cosmetics and pharmaceuticals, for designing hygiene or care products, emulsions constitute an effective method of obtaining a harmonious combination of natural ingredients and different properties in a homogeneous form which is easy to use. The emulsifiers most commonly used at present are alkyl sulphates and sulphonates, alcohols, acids, ethoxylated fatty esters, fatty esters of sorbitan, etc.

Numerous phytosanitary compounds are water-insoluble and, having previously been rendered soluble in an organic solvent, they are capable of being emulsified in water at the time of use or at the moment of formulation with a suitable choice of emulsifiers.

The majority of emulsifiers are found in liquid presentations of phytosanitary products. The emulsifiable concentrate which is the commonest form and still the one most commonly used on the market at present conventionally contains 250 g/l of pesticide, for example, and 50 g/l of emulsifier. It is used by forming a fine emulsion the stability of which has to be ensured for a number of hours irrespective of temperature or the hardness of the water. Concentrated suspensions are a more recent development and correspond to the generation of formulations which allow very low doses to be applied per hectare. This is true, for example, of concentrated emulsions which contain, respectively, 400 to 600 g/l of pesticides and 50 to 100 g/l of emulsifiers. Unlike the two formulations mentioned above, microemulsions are thermodynamically stable systems which are therefore of great interest from the point of view of storage of the products.

The emulsifiers used in the phytosanitary field are essentially when speaking of anionic emulsifiers, calcium dodecyl benzenesulphonate, amine alkylarylsulphonates, ethoxylated fatty esters of alcohol phosphates or ethoxylated alkylphenols. Of the non-ionics, those most commonly used are ethoxylated alkylphenols, alcohols and ethoxylated fatty acids.

The preparation of emulsions using compositions containing polyglycosides and at least one fatty alcohol is well known (WO 92/06778, WO 96/37285, WO 95/13863, WO 98/47610, WO 97/18033, DE 196 07 977).

These emulsifying surfactants may take the form of compositions based on fatty alcohols and polyglycosides which have the advantage of being "self-emulsifying". The term "self-emulsifying" denotes a composition which can be used to produce an emulsion simply, by mixing with gentle shaking with an aqueous phase.

However, it has been found, particularly in EP 0628305, that the use of such emulsifying compositions did not always result in emulsions which were sufficiently stable over time.

The Applicants have also found that the use of emulsifying compositions according to the prior art did not always result in emulsions which were stable in the presence of silicone oils. However, these oils are valuable because they result in emulsions which are pleasant to touch, giving good penetration and generally water-resistant.

It is therefore proposed according to the present invention to use emulsifiers based on polyglycosides and fatty alcohols to obtain stable emulsions (i.e. which do not separate out after the three months storage at 45° C.) even when using less than 5% by weight, based on the total weight of the emulsion, of these emulsifiers, even in the presence of silicone oils.

The high stability of the emulsions has been achieved by using emulsifiers based on fatty alcohol and polyglycosides containing polypentosides selected from among the polyarabinosides, and polyxylosides in specific proportions.

Moreover, the Applicants have found that the emulsions according to the invention, prepared from emulsifier based on fatty alcohol and polyglycosides, had a good suspending power, i.e. they were capable of holding solid particles in suspension, regardless of the viscosity of the emulsion.

In addition, the emulsifiers according to the invention, made up of polyglycosides and fatty alcohols, are of natural origin. They make it possible to prepare stable emulsions of totally plant origin. They do not have the drawbacks of emulsifiers based on polyoxyethylenated compounds which are capable of containing dioxane residues. They are non-irritant, non-toxic and biodegradable.

Moreover, the emulsifiers according to the invention can be used as self-emulsifying compositions.

The present invention thus relates to emulsions containing, by weight:

4.5 to 99.5% of water 0 to 95% of oil 0 to 50% of active substance an emulsifier making up the total of 100%, the emulsifier contains 30 to 65% by weight of at least one fatty alcohol of formula ROH, where R is a straight-chained or branched aliphatic radical, which may be saturated or unsaturated, having 1 to 4 ethylenic unsaturations, having 12 to 22 carbon atoms, the remainder consisting, except for impurities, of:

a) either a mixture of polyglycosides comprising polypentosides of formula (I):

$$R^1O(P)_{n1} \qquad (I)$$

wherein $R^1$ is a straight-chained or branched, saturated or unsaturated aliphatic radical having 1 to 4 ethylenic unsaturations, with 12 to 22 carbon atoms, P is the residue of a pentose selected from arabinose and xylose, n1 is between 1 and 5; and polyhexosides of formula (II):

$$R^2O(H)_2 \qquad (II)$$

wherein $R^2$ is a straight-chained or branched, saturated or unsaturated aliphatic radical having 1 to 4 ethylenic unsaturations, with 12 to 22 carbon atoms, H is the residue of a hexose, n2 is between 1 and 5;

b) either a mixture of polyglycosides of formula (III):

$$R^3O(G_1)_a(G_2)_b(G_3)_c(G_4)_d(G_5)_e \qquad (III)$$

wherein $R^3$ is a straight-chained or branched, saturated or unsaturated aliphatic radical having 1 to 4 ethylenic unsaturations and 12 to 22 carbon atoms, $G_1$, $G_2$, $G_3$, $G_4$ and $G_5$ independently of one another are residues of an ose selected from among the hexoses and pentoses, the latter being selected from arabinose and xylose; a, b, c, d and e being equal to 0 or 1, the sum of a, b, c, d and e being at least 1 c) or a mixture of a and b characterised by the following two features 1 and 2:

1) when the emulsifier contains polyglycosides comprising polypentosides of formula (I) and polyhexosides of formula (II), the polypentosides of formula (I) represent 66 to 100% by weight of the total polyglycosides, and the polyhexosides of formula (II) constitute 0 to 34% by weight of the total polyglycosides, when the emulsifier comprises polyglycosides of formula (III), the pentoses then constitute 66 to 100% by weight based on the total oses $G_1$, $G_2$, $G_3$, $G_4$ and $G_5$ and the hexoses constitute from 0 to 34% by weight based on the total oses $G_1$, $G_2$, $G_3$, $G_4$ and $G_5$ and 2-a) either the emulsifier constitutes at least 2.5% of total weight of the emulsion. The oily phase of the emulsion may thus consist of an oil selected from among:

oils of vegetable origin such as sweet almond oil, coconut oil, castor oil, jojoba oil, olive oil, rape seed oil, groundnut oil, hazel nut oil, palm oil, shea tree butter, apricot kernel oil, calophyllum oil, safflower oil, avocado oil, walnut oil, blackcurrant seed oil, wheatgerm oil, sunflower oil, corn seed oil, soya oil, cotton seed oil, alfalfa oil, barley oil, grapeseed oil, poppy oil, pumpkin oil, sesame oil, rye oil, evening primrose oil, passionflower oil, derivatives of these oils such as hydrogenated oils, oils of animal origin (tallow, fish oils . . . ), mineral oils such as paraffin oil, vaseline oil and mineral oils obtained particularly from petroleum fractions.

synthetic oils such as poly-α-olefines, lanolin derivatives, alkanediols having 2 to 10 carbon atoms such as 1,2-propanediol, 1,3-butanediol, alcohols of formula $R^4$—OH where $R^4$ is a straight-chained or branched, saturated or unsaturated aliphatic radical having 1 to 4 ethylenic unsaturations and 12 to 22 carbon atoms, such as myristic alcohol, cetyl alcohol, stearyl alcohol and oleic alcohol, polyethylene glycols or polypropylene glycols, fatty esters of formula $R^5$—O—CO—$R^6$ wherein $R^5$ and $R^6$ independently of each other denote straight-chained or branched, saturated or unsaturated aliphatic radicals having 1 to 4 ethylenic unsaturations, with 1 to 22 carbon atoms, such as alkyl myristates, particularly butyl myristate, propyl myristate, alkyl palmitates such as isopropyl palmitate, alkyl stearates, particularly hexadecyl stearate, alkyl oleates, particularly dodecyl oleate, alkyl laurates, particularly hexyl laurate, propylene glycol dicaprylate, ethyl-2-hexyl cocoate, esters of lactic acid, behennic acid, isostearic acid such as isostearyl isostearate, and silicone oils including the cyclic polydimethylsiloxanes, the α-ω-hydroxylated polydimethylsiloxanes, the α-ω-trimethylsilylated polydimethylsiloxanes, the polyorganosiloxanes such as the polyalkylmethylsiloxanes, the polymethylphenyl-siloxanes, the polydiphenylsiloxanes, the amino derivatives of silicones, the silicone waxes, the silicone copolyethers (such as the oil SILBIONE 70646® sold by RHONE-POULENC or DC 190® sold by DOW CORNING) or mixed derivatives of silicones such as the mixed copolymers polyalkylmethylsiloxanes-silicones copolyethers.

2-b) or the emulsifier constitutes from 1 to 2.5% of the total weight of the emulsion and the oil is selected from among:

sweet almond oil, coconut oil, castor oil, jojoba oil, olive oil, rape seed oil, groundnut oil, hazelnut oil, palm oil, apricot kernel oil, calophyllum oil, safflower oil, avocado oil, blackcurrant seed oil, sunflower oil, corn seed oil, soya oil, cotton seed oil, alfalfa oil, barley oil, grapeseed oil, poppy oil, pumpkin oil, sesame oil, rye oil, evening primrose oil, passionflower oil, derivatives of these oils, hydrogenated oils, oils of animal origin (tallow, fish oils . . . ), synthetic oils, poly-α-olefines, lanolin derivatives, alkanediols having 2 to 10 carbon atoms, alcohols of formula $R^4$—OH where $R^4$ is a straight-chained or branched, saturated or unsaturated aliphatic radical having 1 to 4 ethylenic unsaturations and 12 to 22 carbon atoms, polyethylene glycols, polypropylene glycols, the fatty esters of formula $R^5$—O—$R^6$ wherein $R^5$ and $R^6$ independently of each other denote straight-chained or branched, saturated or unsaturated aliphatic radicals having 1 to 4 ethylenic unsaturations, with 1 to 22 carbon atoms, such as alkyl myristates, particularly butyl myristate, propyl myristate, alkyl palmitates such as isopropyl palmitate, alkyl stearates, particularly hexadecyl stearate, alkyl oleates, particularly dodecyl oleate, alkyl laurates, particularly hexyl laurate, propylene glycol dicaprylate, ethyl-2-hexyl cocoate, esters of lactic acid, behennic acid, isostearic acid such as isostearyl isostearate, and silicone oils including the cyclic polydimethylsiloxanes, the α-ω-hydroxylated polydimethylsiloxanes, the α-ω-trimethylsilylated polydimethylsiloxanes, the polyorganosiloxanes such as the polyalkylmethylsiloxanes, the polymethylphenyl-siloxanes, the polydiphenylsiloxanes, the amino derivatives of silicones, the silicone waxes, the silicone copolyethers (such as the oil SILBIONE 70646® sold by RHONE-POULENC or DC 190® sold by DOW CORNING) or mixed derivatives of silicones such as the mixed copolymers polyalkylmethylsiloxanes-silicones copolyethers.

Generally speaking, when the emulsifier constitutes at least 2.5% of the total weight of the emulsion, emulsions containing 10 to 30% of oil based on the total weight of the emulsion are preferred on account of their pleasant touch.

The emulsions according to the present invention may also contain an emulsifier which complements the emulsifying agent comprising at least one fatty alcohol and a glycoside of the invention, so that the total quantity of emulsifier is less than 25% based on the total weight of the emulsion. However, on account of the great efficacy of the emulsifiers based on fatty alcohol and polyglycosides according to the invention, it is preferable to use as emulsifier only the one according to the present invention.

Generally, the total quantity of emulsifier will be less than 25% of the total weight of the emulsion and will preferably constitute 2.5 to 6% and more particularly 2.5 to 4% of the total weight of the emulsion.

According to an advantageous feature, linked particularly with their excellent stability and good suspending power, emulsions containing emulsifiers based on polyglycosides containing 80 to 100% and more particularly 97 to 100% by weight of polypentosides and 0 to 20% and more particularly 0 to 3% by weight of polyhexosides are preferred.

The term emulsion having a great suspending power denotes an emulsion which is capable of holding in suspension, in well dispersed manner, solid particles having an average size of 50 µm to 500 µm after storage for 3 months at 45° C. and centrifugation at 2000 rpm for 3 minutes at 20° C.

Each ose group may be in the a or β isomeric form, in the L or D form and in the furanose or pyranose form. Hexoses of series D are preferred, notably D-glucose, D-galactose and D-mannose. Of the pentoses, L-arabinose and D-xylose are preferred which are found in abundance in the hemicelluloses of numerous plants.

Because of the fact that glucose is abundant on the sugar market, glucosides preferably make up at least 80% of the polyhexosides. For the same reasons, advantageously, the polyxylosides represent 85% and preferably 98% by weight of the polypentosides.

Fatty alcohols of formula ROH having 14 to 22 carbon atoms and notably mixtures of hexadecanol and octadecanol and mixtures of tetradecanol and octadecanol are particularly preferred.

Moreover, on account of their speed of manufacture, the compositions of the invention containing polyglycosides wherein the radicals $R^1$ and $R^2$ or the radical $R^3$ are identical to the radical R of the fatty alcohol are particularly preferred.

On account of their effectiveness and ease of manufacture, emulsifiers containing 40 to 60% by weight of fatty alcohols based on the total weight of emulsifier and preferably 47 to 52% of fatty alcohol, the remainder being polyglycosides, with the exception of any impurities, are most particularly preferred.

The emulsifiers based on polyglycosides and fatty alcohols may be prepared by simply mixing their components together in proportions as specified above. The homogenisation techniques used are those currently used for mixing solid or liquid ingredients. For solid ingredients it is, however, preferable if possible to mix them at a temperature above their melting points in liquid form.

The emulsifiers may be prepared using one of the two methods conventionally used for synthesising alkyl polyglycosides.

The first method consists in directly contacting the reducing sugar and the fatty alcohol in the presence of an acid catalyst to obtain the polyglycosides.

The second method consists, in a first step, of carrying out glycosidation with a short alcohol corresponding to the formula $R^7OH$, where $R^7$ is a $C_{1-5}$-alkyl radical. In a second step, transglycosidation is carried out, which consists of displacing the short alcohol of formula $R^7OH$ with a fatty alcohol.

Each of these two methods may be completed, if required, by operations of neutralisation, filtration, elimination of the excess fatty alcohol and decolorisation.

Advantageously, particularly when using crystalline reducing sugars as starting materials, it is preferable to use the first direct method which has the advantage of being quicker and easy to carry out. However, when reducing sugars in the form of syrups are used, it is preferable to use the second method which produces a more homogeneous reaction medium and consequently polyglycosides of better quality which contain no or very few breakdown products.

The term reducing sugars denotes hexoses, pentoses and the corresponding oligosaccharides having a free anomeric hydroxyl.

During the direct glycosidation of sugars with fatty alcohol or a mixture of fatty alcohols, or during transglycosidation if the grafting is carried out in two steps, the fatty alcohol is preferably used in excess (1 to 3 and preferably 1.5 to 2.5 molar equivalents based on the reducing sugars), so that the reaction product contains the quantities of free fatty alcohol and polyglycosides specified hereinbefore.

It would also be possible to eliminate the fatty alcohol or mixture of fatty alcohols totally or partially at the end of the synthesis and then add specified proportions of a fatty alcohol or a mixture of fatty alcohols which is different or identical to those used during synthesis in order to obtain the emulsifier according to the invention.

However, the first solution is preferred, which consists in using the excess fatty alcohol so that the reaction product contains the specified amounts of fatty alcohols and polyglycosides.

In practice, there are three main methods of obtaining the emulsifiers according to the invention from reducing sugars and fatty alcohols.

The first method consists in carrying out the glycosidation of the reducing sugars separately (hexoses such as glucose, galactose, mannose and the corresponding oligosaccharides, pentoses selected from among arabinose and xylose and the corresponding oligosaccharides) by contacting them with one or more fatty alcohols in the presence of an acid catalyst conventionally used for reactions of glycosylation. It is preferable to use the fatty alcohol in excess (1 to 3 and preferably 1.5 to 2.5 molar equivalents based on the reducing sugars) so that the reaction product contains the specified amounts of free fatty alcohol and polyglycosides. After neutralisation of the acid catalyst, the polypentosides of formula (I):

$$R^1O(P)_{n1} \qquad (I)$$

and the polyhexosides of formula (II) are obtained:

$$R^2O(H)_{n2} \qquad (II).$$

Then, 66 to 100%, advantageously 80 to 100% and preferably 97 to 100% by weight of polypentosides, based on the total weight of polyglycosides, and 0 to 34%, advantageously 0 to 20% and preferably 0 to 3% by weight of polyhexosides, based on the total weight of the polyglycosides, are mixed in the presence of fatty alcohol of formula ROH, if necessary, in order to obtain the emulsifiers according to the invention.

The second method comprises mixing 66 to 100%, advantageously 80 to 100% and preferably 97 to 100% by weight of pentoses and/or the corresponding oligosaccharides, based on the total weight of reducing sugars, with 0 to 34%, advantageously 0 to 20% and preferably 0 to 3% by weight, based on the total weight of reducing sugars, of hexoses and/or the corresponding oligosaccharides and carrying out glycosidation of the mixture of reducing sugars thus obtained. The glycosylation is carried out in the presence of an acid catalyst with an excess (1 to 3 and preferably 1.5 to 2.5 molar equivalents in relation to the reducing sugars) of fatty alcohol so that the reaction product preferably contains the specified amounts of free fatty alcohols. The reaction product is neutralised and if necessary the fatty alcohol of formula ROH is added in order to obtain the specifications given above.

Finally, the third method consists in using syrups of mixtures of the reducing sugars derived from raw plant materials rich in starch and hemicellulose containing 66 to 100%, preferably 80 to 100% and more particularly 97 to 100% of pentoses and 0 to 34%, preferably 0 to 20% and more particularly 0 to 3% of hexoses and carrying out glycosidation of these syrups of reducing sugars with fatty alcohols in order to obtain the emulsifiers according to the invention.

According to an advantageous feature of the invention, connected in particular with the ease of industrial synthesis, the very great reactivity of pentoses compared with glucose during the reaction of glycosylation (cf. WO 9729115) and the natural abundance of D-xylose, particularly preferred emulsions are those containing an emulsifier prepared by bringing crystalline D-xylose into direct contact with 1 to 3 and preferably 1.5 to 2.5 molar equivalents, based on xylose, fatty alcohol or a mixture of fatty alcohols of formula ROH, so that the reaction product contains the quantities of fatty alcohol and polyglycosides specified hereinbefore, in the presence of an acid catalyst such as sulphuric acid, a sulphonic acid such as methanesulphonic acid, hydrochloric acid, hypophosphorous acid or any other acid catalyst for carrying out glycosidation and mixtures thereof, at a temperature of between 50 and 100° C. and preferably between 80 and 90° C. The acid catalyst is then neutralised. Neutralisation is carried out, for example, using an alkali metal or alkaline earth metal hydrogen carbonate or carbonate, notably sodium hydrogen carbonate, an alkali metal or alkaline earth metal hydroxide, notably sodium hydroxide, or an organic base such as triethanolamine. If required, the insoluble matter can then be filtered off or some or all of the free fatty acid may be evaporated. The emulsifier obtained is colourless and free from breakdown products. At the end of the synthesis, depending on the fatty alcohol or mixture of fatty alcohols used, it takes the form of a solid, paste-like or liquid wax. Starting from a solid wax it is possible to obtain powder, flakes or beads or pastilles, particularly for ease of use at a later stage. It is preferable to isolate the composition in the form of hemispherical pastilles about 2 mm in diameter and 0.7 mm thick, which are very easy to use thereafter, notably for the production of emulsions.

Of course, the emulsions according to the invention comprising an emulsifier containing at least one fatty alcohol and polyglycosides may also contain 0 to 50% of one or more active substances such as conventional cosmetic, lipophilic or hydrophilic adjuvants, especially those which are already currently used in the manufacture and production of emulsions. Of the conventional cosmetic adjuvants which may be contained in the aqueous phase and/or fatty phase of the emulsions, the following may be mentioned in particular:

- ionic or non-ionic thickeners and gelatinising agents such as cellulose derivatives (carboxymethylcellulose, hydroxyethylcellulose), guar (hydroxypropylguar, carboxymethylguar, carboxymethylhydroxypropylguar), carob, tree exsudates (gum arabic, karaya), seaweed extracts (alginates, carrageenates), exudates of microorganisms (xanthane gum),
- hydrotropic agents such as short $C_{2-8}$-alcohols, particularly ethanol, diols and glycols such as diethyleneglycol, dipropyleneglycol, etc.
- hydrating agents (or skin moisturisers such as glycerol, sorbitol, collagen, gelatin, aloe vera, hyaluronic acid, urea or skin protecting agents such as proteins or protein hydrolysates, cationic polymers such as cationic derivatives of guar (JAGUAR C13S®, JAGUAR C162®, HICARE 1000® marketed by RHONE-POULENC),
- glycolipids such as lipid sophoroses,
- mineral powders or particles such as calcium carbonate, mineral oxides in the form of powder or in colloidal form (particles smaller than or of the order of one micron, sometimes several tens of nanometres) such as titanium dioxide, silica, aluminium salts generally used as anti-perspirants, kaolin, talc, clays and derivatives thereof, . . .
- preservatives, such as the methyl, ethyl, propyl and butyl esters of p-hydroxybenzoic acid, sodium benzoate, GERMABEN® or any other chemical agent which prevents bacterial proliferation or mould and is traditionally used in cosmetic compositions, are generally added to these compositions in amounts of 0.01 to 3% by weight.

Instead of these chemical agents it is sometimes possible to use agents which modify the activity of water and greatly increase the osmotic pressure, such as carbohydrates or salts.

- organic sun filters which are active in UV-A and/or UV-B for protecting the skin or hair from the effects of the sun and UV radiation, such as the compounds authorised in European Directive No. 76/768/EEC, the annexes thereto and subsequent amendments to this directive,
- photoprotective mineral monopigments such as titanium dioxide or cerium oxides in the form of powder or colloidal particles.
- softeners, antioxidants, self-tanning agents such as DHA, insect repellant agents, vitamins, perfumes, fillers, sequestering agents, dyes, buffers, etc.
- abrasives such as ground apricot kernels, micro-beads, . .

The emulsions prepared from the emulsifier according to the invention may be used in various cosmetic or dermatological applications, for example in the form of creams for the face, body, scalp or hair or in the form of body lotions or makeup removing lotions or in the form of ointments for pharmaceutical use, for example. These emulsions may also be used for makeup, notably in the form of foundations after the addition of pigments. They may also be used as sun creams after the addition of UVA and/or UVB and/or DHA filters or as after-sun creams or lotions after the addition of soothing compounds such as panthenol.

The emulsions may also contain ionic or non-ionic surfactants with a washing, foaming or detergent action such as sodium laurylether sulphate, alkyl betaines, APGs, for producing washing emulsions such as moisturising washing creams or emulsions for shaving.

The emulsions may also contain, with a view to improving their cosmetic qualities, a cosmetic wax such as rice wax, candellila wax or Japan wax. The proportion of wax is generally between 0.5 and 3%, preferably between 1 and 2% by weight, based on the total weight of the emulsion.

The emulsifying agents based on polyglycosides and fatty alcohols according to the invention may also be used in formulations where finely divided solids have to be kept suspended in water, e.g. formulations of agrochemical active substances (herbicides, insecticides, fungicides, etc.) known under the generic title of "concentrated suspensions". Apart from a dispersant or emulsifier used in an amount from 1 to 50 g/l, the additives found in a concentrated suspension formulation are additives such as those described in the commercial brochure "Auxiliaries for agrochemical formulations" edited by RHONE-POULENC GERONAZZO SpA. One might mention, for example, a wetting surfactant chosen from among the alkyl derivatives of aryl aliphatic alcohols, the aryl sulphonate derivatives such as sodium isopropylnaphthalene sulphonate marketed under the name SUPRAGIL WP® by RHONE-POULENC GERONAZZO, the dialkylsulphosuccinates such as sodium di-ethyl-2 hexylsulphosuccinate, dispersant polymers such as polyacrylic acids and the salts thereof, copolymers of maleic anhydride (or acid) and diisobutylene and the salts thereof such as GEROPON T36® (RHONE-POULENC GERONAZZO), the condensed sodium methyl naphthalenesulphonates such as SUPRAGIL MNS90® (RHONE-POULENC GERONAZZO), the dispersant polymers derived from lignin such as sodium lignosulphonates or calcium lignosulphonates or other dispersant surfactants such as alkoxylated, optionally sulphated or phosphated derivatives of tristyrylphenols. These formulations may also contain anti-freeze additives such as propylene glycol and thickeners which modify the rheological behaviour of the suspension, such as xanthane gum, cellulose derivatives (carboxymethylcellulose), guar gum or derivatives thereof, clays or modified clays such as bentonite and bentones. Of the active substances which may be formulated in this way, those generally used have a melting point greater than 45° C., preferably above 60° C. with a water solubility of less than 10 g/l, preferably less than 1 g/l. The active substances for plant protection involved here are herbicides, fungicides and insecticides such as those described in THE PESTICIDE MANUAL (9th Edition, C. R. WORKLING and R. J. HANCE, editors, published by The British Crop Protection Council) which meet the criteria described above.

The emulsifiers based on polyglycosides and fatty alcohols according to the invention may also be used in plant-protection formulations such as emulsifiable concentrates, concentrated suspensions, concentrated emulsions, microemulsions or suspo-emulsions. They are used in concentrations of between 5 and 150 g/l. The active plant-protecting substances may be those described hereinbefore for concentrated suspensions. The emulsifiers of the present invention are particularly effective for preparing plant protecting concentrated emulsions. The active substance is suspended in water using the emulsifier, which ensures the stability of the concentrate during storage as well as the spontaneity and stability of the diluted emulsion when it is used. Typical compositions are made up of about 40 to 80% of active substance, such as for example fatty acid esters such as methylesters of rape seed (EMC) marketed by Robbe and 1 to 15% of additives. This form provides ease of use of the emulsifiable concentrates, with the major advantage of an aqueous carrier instead of a solvent, which provides greater safety.

The emulsifying agents according to the present invention are also effective in the preparation of gas oil emulsions used as diesel fuel. They allow water to be incorporated in the fuel, thereby reducing the omissions of toxic combustion gases. These emulsions are generally made up to 60 to 97% of gas oil, 2.5 to 39.5% of water and 0.5 to 5% of emulsifier. They may also contain the additives currently used in diesel-type fuels.

Four main methods of producing emulsions are proposed:

The first consists in heating all the ingredients at the same time to a temperature of between 50 and 90° C. and particularly between 70 and 75° C., then homogenising with a blade-type rotary stirrer rotating at 500 to 15000 rpm, particularly at 1000 to 2000 rpm, at a temperature of between 50 and 90° C., and then cooling, with gentle stirring (from 100 to 1000, particularly from 300 to 500 rpm) down to a temperature of the order of 25° C. If homogenisation is lively when heated, it is not always advisable to stir the emulsion during cooling.

The second consists in working by phase inversion. In this case, the lipophilic and hydrophilic phases are heated separately to a temperature of between 50 and 90° C. The lipophilic phase, which contains the composition according to the invention, is stirred vigorously with a blade-type rotary stirrer rotating at 500 to 15000 rpm, particularly 1000 to 2000 rpm, and the hydrophilic phase is slowly added to this phase at a rate such that the hydrophilic phase is instantly absorbed by the lipophilic phase, until phase inversion occurs, characterised by an abrupt change in viscosity. The addition may then be carried out more rapidly at a rate such that the hydrophilic phase stagnates for 1 to 3 seconds above the lipophilic phase if it is being added from above. The emulsion is then left to cool with gentle stirring (100 to 1000, particularly 300 to 500 rpm) down to a temperature of the order of 25° C.

The third method is carried out by dispersion. In this case, the lipophilic phase (which contains the emulsifier according to the invention) and the hydrophilic phase are heated separately to a temperature of between 50 and 90° C. and preferably to between 70 and 75° C. The hydrophilic phase is stirred with a blade-type rotary stirrer rotating at 500 to 15000 rpm, particularly 1000 to 2000 rpm, and the lipophilic phase is progressively added thereto at a rate such that the lipophilic phase is instantly absorbed by the hydrophilic phase. The emulsion is then left to cool with gentle stirring (at 100 to 1000, particularly 300 to 500 rpm) down to a temperature of the order of 25° C.

The fourth method consists in heating all the ingredients at the same time to a temperature between 50 and 90° C., then homogenising them with a blade-type rotary agitator rotating at 100 to 1000 rpm and passing the resulting mixture through a "high pressure" homogeniser once or a number of times. "High pressure" homogenisers are apparatus which allow the mixture being emulsified to be subjected to pressures ranging from 10 to 1000 bar and particularly 50 to 500 bar.

According to another aspect of the invention, the composition based on polyglycosides may be used as a self-emulsifying base for the preparation of emulsions by hot dispersion of the compositions according to the invention, e.g. at about 50 to 90° C., in water or a suitable polar medium, by simple agitation, notably mechanical or by sonication. If the composition is dispersed in water by agitation or by sonication at a temperature close to the melting point of the emulsifier, dispersions rich in vesicles are obtained.

The two main evaluation criteria which demonstrate the good stability of the emulsions obtained with the 30 emulsifiers according to the present invention are as follows:

The resistance to centrifugation by determining the foaming index, which is defined as the percentage by volume of residual foamed emulsion after a treatment of destabilisation by centrifugation at 4080 g for 1 hour at 25° C. The more extreme the percentage of foamed emulsion, the better the result. After centrifugation, the foaming index is the ratio of the volume of residual emulsion over the total volume of initial emulsion multiplied by 100.

Monitoring the retrodiffusion of the emulsions by means of a vertical scanning macroscopic analyser such as the "TURBISCAN 2000". In fact, the instability of the emulsions is often the result of a combination of physical processes implying two main types of phenomena, in particular:

An increase in the size of the droplets or aggregates (coalescence, flocculation).

The migration of the droplets into the sample (foaming, sedimentation).

The foaming and sedimentation are sometimes regarded as harmless phenomena whereas coalescence is always disastrous for the formulator on account of being irreversible. It therefore appears to be important to detect these phenomena at a very early stage (to reduce the ageing tests which are at least 90 days at 45° C.) and identify them. The method of evaluating the stability of the emulsions proposed here makes it possible to detect local variations in the concentrations and/or sizes of the particles in a concentrated medium well before the naked eye can. This technique also allows us to obtain information as to the type or types of physical processes involved in the destabilisation of the mixture and the order of their appearance. The most stable emulsions are those which have the smallest variation in retrodiffusion as a function of time.

In order to evaluate the good suspending power of the emulsions according to the present invention, we have prepared them by adding, as additives, solid particles ranging in size from 0.05 to 0.250 mm. We then subjected the emulsions to a destabilising treatment by centrifuging at 2000 rpm for 3 minutes at 20° C. We then measured the deposit of solid particles left at the bottom of the tube. The results are expressed as a percentage of the deposit defined by the volume of the deposit in relation to the total volume of emulsion centrifuged. The emulsions having the best suspending powers are those for which we do not obtain any deposit at all.

The following Examples set out to illustrate the present invention.

SYNTHESIS EXAMPLE 1

Process for Preparing Tetradecyl and Octadecyl Polyglucosides 140 g of hydrous D-glucose are suspended in 371 g of fatty alcohol (tetradecanol: 25%, octadecanol: 75%) containing 2.80 g of sulphuric acid. The reaction medium is kept under reduced pressure for 3 hours at 100° C. After filtering, the acidity of the medium is neutralised with a 30.5% aqueous sodium hydroxide solution to pH 7 to 8. The reaction product termed the emulsifier based on tetradecyl and octadecyl glucosides (486 g) takes the form of a solid paste which contains 50.5% by weight of residual fatty alcohol. It is then ground to obtain a powder with a particle size of less than 800 μm.

SYNTHESIS EXAMPLE 2

Process for Preparing Cetaryl Polyglucosides 140 g of hydrous D-glucose are suspended in 377.5 g of fatty alcohol (hexadecanol: 33%, octadecanol: 67%) containing 2.80 g of sulphuric acid. The reaction medium is kept under reduced pressure for 3 hours at 100° C. After filtering, the acidity of the medium is neutralised with a 30.5% aqueous sodium hydroxide solution to pH 7 to 8. The reaction product termed the emulsifier based on cetaryl glucosides (492.6 g) takes the form of a solid paste which contains 50.7% by weight of residual fatty alcohol. It is then ground to obtain a powder with a particle size of less than 800 μm.

SYNTHESIS EXAMPLE 3

Process for Preparing Cetaryl Polyglucosides 100 g of hydrous D-glucose are suspended in 264.8 g of fatty alcohol (hexadecanol: 50%, octadecanol: 50%) containing 2 g of sulphuric acid. The reaction medium is kept under reduced pressure for 3 hours at 100° C. After filtering, the acidity of the medium is neutralised with a 30.5% aqueous sodium hydroxide solution to pH 7 to 8. The reaction product termed the emulsifier based on cetaryl glucosides (335 g) takes the form of a solid paste which contains 50.5% by weight of residual fatty alcohol. This is then adjusted to 55%, based on the total reaction product, by the addition of a mixture of hexadecanol and octadecanol (50/50) and is ground to obtain a powder with a particle size of less than 800 μm.

EXAMPLE 1

Process for Preparing an Emulsifier Based on Polyxylosides and Fatty Alcohol According to the Invention 140 g of 97% pure anhydrous D-xylose are suspended in 478 g of fatty alcohol (tetradecanol: 25%, octadecanol: 75%) containing 4.2 g of sulphuric acid. The reaction medium is kept under reduced pressure for 3 hours at 90° C. After filtration, the acidity of the medium is neutralised with a 30.5% aqueous sodium hydroxide solution to give a pH of 7 to 8. The reaction product termed emulsifier based on alkyl polyxylosides (590 g) is in the form of a solid paste which contains 49.5% by weight of residual fatty alcohol. It is ground to obtain a powder with a particle size of less than 800 μm.

EXAMPLE 2

Process for Preparing an Emulsifier Based on Polyxylosides and Fatty Alcohol According to the Invention 100 g of 97% pure anhydrous D-xylose are suspended in 340.6 g of fatty alcohol (hexadecanol: 33%, octadecanol: 67%) containing 3.0 g of sulphuric acid. The reaction medium is kept under reduced pressure for 1.5 hours at 90° C. After filtration, the acidity of the medium is neutralised with a 30.5% aqueous sodium hydroxide solution to give a pH of 7 to 8. The reaction product termed emulsifier based on alkyl polyxylosides (408 g) is in the form of a solid paste which contains 53% by weight of residual fatty alcohol. It is ground to obtain a powder with a particle size of less than 800 μm

EXAMPLE 3

Process for Preparing an Emulsifier Based on Cetaryl Polyxylosides and Fatty Alcohol According to the Invention 140 g of 97% pure anhydrous D-xylose are suspended in 488 g of fatty alcohol (hexadecanol: 30%, octadecanol: 70%) containing 4.2 g of sulphuric acid. The reaction medium is kept under reduced pressure for 3 hours at 90° C. After filtration, the acidity of the medium is neutralised with a 30.5% aqueous sodium hydroxide solution to give a pH of 7 to 8. The reaction product termed emulsifier based on cetaryl polyxylosides (600 g) is in the form of a solid paste which contains 50% by weight of residual fatty alcohol. It is ground to obtain a powder with a particle size of less than 800 μm.

EXAMPLE 4

Process for Preparing an Emulsifier Based on Polyxylosides and Fatty Alcohol According to the Invention 140 g of 97% pure anhydrous D-xylose are suspended in 478 g of fatty alcohol (hexadecanol: 30%, octadecanol: 70%) containing 4.2 g of sulphuric acid. The reaction medium is kept under reduced pressure for 3 hours at 90° C. After filtration, the acidity of the medium is neutralised with a 30.5% aqueous sodium hydroxide solution to give a pH of 7 to 8. The reaction product termed emulsifier based on alkyl polyxylosides (572 g) is in the form of a solid paste which contains 50% by weight of residual fatty alcohol. It is ground to obtain a powder with a particle size of less than 800 μm.

EXAMPLE 5

Process for Preparing Tetradecyl and Octadecyl Polyarabinosides 100 g of anhydrous L-arabinose are suspended in 318 g of fatty alcohol (tetradecanol: 25%, octadecanol: 75%) containing 2.00 g of sulphuric acid. The reaction medium is kept under reduced pressure for 1.5 hours at 90° C. After filtration, the acidity of the medium is neutralised with a 30.5% aqueous sodium hydroxide solution to pH 7 to 8. The reaction product termed emulsifier based on tetradecyl and octadecyl arabinosides (395 g) takes the form of a solid paste which contains 44.5% by weight of residual fatty alcohol. This is then adjusted to 50% based on the total reaction product by the addition of a mixture of tetradecanol and octadecanol (25/75) and is ground to obtain a powder with a particle size of less than 800 μm.

EXAMPLE 6

Process for Preparing Cetaryl Polyarabinosides 100 g of anhydrous L-arabinose are suspended in 324 g of fatty alcohol (hexadecanol: 33%, octadecanol 67%) containing 2.00 g of sulphuric acid. The reaction medium is kept under reduced pressure for 3 hours at 80° C. After filtration, the acidity of the medium is neutralised with a 30.5% aqueous sodium hydroxide solution to pH 7 to 8. The reaction product termed emulsifier based on cetaryl arabinosides (401 g) takes the form of a solid paste which contains 44.7% by weight of residual fatty alcohol. This is then adjusted to 50% based on the total reaction product by the addition of a mixture of hexadecanol and octadecanol (33/67) and is ground to obtain a powder with a particle size of less than 800 μm.

EXAMPLE 7

Process for Preparing an Emulsifier Based on Polyglycoside and Fatty Alcohol According to the Invention 350 g of sugar syrup containing 87.5 g of water, 190 g of D-xylose, 36 g of L-arabinose, 34.5 g of D-glucose and 2 g of D-galactose are added dropwise, over 1 hour 30 minutes, to 394 g of n-butanol containing 5.2 g of sulphuric acid and 54 g of water at a temperature of the order of 100 to 105° C. The water is eliminated during the reaction by azeotropic distillation of the mixture of water and butanol. Then 45% of the reaction medium obtained are added to 366 g of fatty alcohol consisting of 25% tetradecanol and 75% of fatty alcohol derived from rape seed (mixture of hexadecanol: 10% and octadecanol: 90% by weight) containing 1.2 g of sulphuric acid, at a temperature of 90° C. The butanol is continuously eliminated under reduced pressure during the addition. Then, at the same temperature, the acidity of the medium is neutralised with a 30.5% aqueous sodium hydroxide solution to pH 7 to 8 and the product is decolorised in the presence of oxygenated water. After cooling to 20° C. and grinding the solid obtained, 480 g of emulsifier are collected, containing 48% by weight, based on the total weight of the composition, of fatty alcohol.

EXAMPLE 8

Process for Preparing an Emulsifier Based on Polyglycoside and Fatty Alcohol According to the Invention 350 g of sugar syrup containing 87.5 g of water, 190 g of D-xylose, 36 g of L-arabinose, 34.5 g of D-glucose and 2 g of D-galactose are added dropwise, over 1 hour 30 minutes, to 393.5 g of n-butanol containing 5.2 g of sulphuric acid and 53.5 g of water at a temperature of the order of 100 to 105° C. The water is eliminated during the reaction by azeotropic distillation of the mixture of water and butanol. The reaction medium obtained is then added to 837 g of fatty alcohol consisting of 30% hexadecanol and 70% octadecanol containing 2.6 g of sulphuric acid at a temperature 90° C. The butanol is continuously eliminated under reduced pressure during the addition. Then, at the same temperature, the acidity of the medium is neutralised with a 30.5% aqueous sodium hydroxide solution to pH 7 to 8 and the product is decolorised in the presence of oxygenated water. After pelleting, 1061 g of emulsifier are collected, containing 49% by weight of fatty alcohol, based on the total weight of the composition.

EXAMPLE 9

Process for Preparing an Emulsifier Based on Polyglycoside and Fatty Alcohol According to the Invention 20 g of the emulsifier based on tetradecyl and octadecyl polyglucoside according to synthesis Example 1, 68 g of the emulsifier based on tetradecyl and octadecyl polyxylosides according to Example 1 and 12 g of the emulsifier based on tetradecyl and octadecyl polyarabinosides according to Example 5 are mixed together to obtain 100 g of emulsifier based on polyglycosides containing approximately 50% by weight of fatty alcohol, the remainder consisting of tetradecyl and octadecyl polyglycosides containing 80% by weight, based on the polyglycosides, of polypentosides (85% by weight of polyxylosides and 15% by weight of polyarabinosides based on the polypentosides) and 20% by weight of polyhexosides.

EXAMPLE 10

Process for Preparing an Emulsifier Based on Polyglycoside and Fatty Alcohol According to the Invention 34 g of the emulsifier based on cetaryl polyglucoside according to synthesis Example 2, 56 g of the emulsifier based on cetaryl polyxylosides according to Example 2 and 10 g of the emulsifier based on cetaryl polyarabinosides according to Example 6 are mixed together to obtain 100 g of emulsifier based on polyglycosides containing approximately 51% by weight of fatty alcohol, the remainder consisting of cetaryl polyglycosides containing 66% by weight, based on the polyglycosides, of polypentosides (85% by weight of polyxylosides and 15% by weight of polyarabinosides based on the polypentosides) and 34% by weight of polyhexosides.

EXAMPLE 11

Process for Preparing an Emulsifier Based on Polyglycoside and Fatty Alcohol According to the Invention 20 g of the emulsifier based on tetradecyl and octadecyl polyglucoside according to synthesis Example 1 and 180 g of the emulsifier based on tetradecyl and octadecyl polyxylosides according to Example 1 are mixed together to obtain 200 g of emulsifier based on polyglycosides containing about 50% by weight of fatty alcohol, the remainder consisting of tetradecyl and octadecyl polyglycosides containing 90% by weight, based on the polyglycosides, of polypentosides (polyxylosides) and 10% by weight of polyhexosides (polyglucosides).

EXAMPLE 12

Process for Preparing an Emulsifier Based on Polyglycoside and Fatty Alcohol According to the Invention 115 g of D-xylose, 20 g of L-arabinose and 15 g of D-glucose are placed in 235 g of 96% ethanol containing 3 g of sulphuric acid. The medium is refluxed for 3 hours. Then the reaction medium obtained is added to 583 g of fatty alcohol consisting of 30% hexadecanol and 70% octadecanol containing 1.5 g of sulphuric acid at a temperature of 90° C. The ethanol is eliminated continuously under reduced pressure during the addition. Then, at the same temperature, the acidity of the medium is neutralised with a 30.5% aqueous sodium hydroxide solution to pH 7 to 8. After pelleting, 701 g of emulsifier are collected, containing 58% by weight of fatty alcohol, based on the total weight of the composition.

EXAMPLE 13

Process for Preparing an Emulsifier Based on Polyglycoside and Fatty Alcohol According to the Invention 30 g of the emulsifier based on tetradecyl and octadecyl polyglucoside according to synthesis Example 1 and 70 g of the emulsifier based on tetradecyl and octadecyl polyxylosides according to Example 1 are mixed together to obtain 100 g of emulsifier based on polyglycosides containing about 50% by weight of fatty alcohol, the remainder consisting of tetradecyl and octadecyl polyglycosides containing 70% by weight, based on the polyglycosides, of polypentosides (polyxylosides) and 30% by weight of polyhexosides (polyglucosides).

EXAMPLE 14

Process for Preparing an Emulsifier Based on Polyglycoside and Fatty Alcohol According to the Invention 91 g of D-xylose, 56 g of L-arabinose and 53.9 g of D-glucose monohydrate are suspended in 803 g of fatty alcohol (hexadecanol: 50%, octadecanol: 50%) containing 6 g of sulphuric acid. The reaction medium is kept under reduced pressure for 2 hours at 100° C. After filtration, the acidity of the medium is neutralised with a 30.5% aqueous sodium hydroxide solution to pH 7 to 8. The reaction product termed the emulsifier based on alkyl polyglycosides (960 g) takes the form of a solid paste which contains 56% by weight of residual fatty alcohol. It is ground in order to obtain a powder with a particle size of less than 800 μm.

EXAMPLE 15

Process for Preparing an Emulsifier Based on Polyglycoside and Fatty Alcohol According to the Invention 200 g of sugar syrup containing 25% of water, 108 g of D-xylose, 21 g of L-arabinose 20, g of D-glucose and 1 g of D-galactose are added dropwise, over 1 hour, to 208 g of n-butanol containing 3 g of sulphuric acid and 14 g of water at a temperature of the order of 100 to 105° C. The water is eliminated during the reaction by azeotropic distillation of the mixture of water and butanol. The reaction medium obtained is then added to 423 g of fatty alcohol consisting of 80% tetradecanol and 20% octadecanol containing 1.5 g of sulphuric acid at a temperature 90° C. The butanol is continuously eliminated under reduced pressure during the addition. Then, at the same temperature, the acidity of the medium is neutralised with a 30.5% aqueous sodium hydroxide solution to pH 7 to 8 and the product is decolorised in the presence of oxygenated water. After cooling to 20° C. and grinding the solid obtained, 572 g of emulsifier are collected which contains 47.5% by weight of fatty alcohol, based on the total weight of the composition.

EXAMPLE 16

Process for Preparing an Emulsifier Based on Polyglycoside and Fatty Alcohol According to the Invention 200 g of sugar syrup containing 25% of water, 108 g of D-xylose, 21 g of L-arabinose, 20 g of D-glucose and 1 g of D-galactose are added dropwise, over 1 hour, to 208 g of n-butanol containing 3 g of sulphuric acid and 14 g of water at a temperature of the order of 100 to 105° C. The water is eliminated during the reaction by azeotropic distillation of the mixture of water and butanol. The reaction medium obtained is then added to 423 g of fatty alcohol consisting of 60% tetradecanol 5 and 40% octadecanol containing 1.5 g of sulphuric acid at a temperature 90° C. The butanol is continuously eliminated under reduced pressure during the addition. Then, at the same temperature, the acidity of the medium is neutralised with a 30.5% aqueous sodium hydroxide solution to pH 7 to 8 and the product is decolorised in the presence of oxygenated water. After cooling to 20° C. and grinding the solid obtained, 582 g of emulsifier are collected which contains 47% by weight of fatty alcohol, based on the total weight of the composition.

EXAMPLE 17

Process for Preparing Cetaryl Polyxylosides 100 g of D-xylose are suspended in 318 g of fatty alcohol (hexadecanol: 50%, octadecanol: 50%) containing 2 g of sulphuric acid. The reaction medium is kept under reduced pressure for 3 hours at 80° C. After filtering, the acidity of the medium is neutralised with a 30.5% aqueous sodium hydroxide solution to pH 7 to 8. The reaction product termed the emulsifier based on cetaryl polyxylosides (400 g) takes the form of a solid paste which contains 43% by weight of residual fatty alcohol. This is then adjusted to 55% based on the total reaction product by adding a mixture of hexadecanol and octadecanol (50/50) and is ground to obtain a powder with a particle size of less than 800 µm.

EXAMPLE 18

Example of Fluid Emulsion According to the Invention 2 g of the emulsifying agent of Example 1 are suspended in 48 g of water obtained by osmosis. The mixture is heated to 50° C. and then stirred (at 500 rpm) for 2 minutes. The emulsion thus formed is then cooled to ambient temperature. This emulsion remains stable for 3 months in a drying cupboard at 45° C.

EXAMPLE 19

Example of Fluid Emulsion According to the Invention 1.5 g of the emulsifying agent of Example 2 are suspended in 48.5 g of water obtained by osmosis. The mixture is heated to 50° C. and then stirred (at 500 rpm) for 2 minutes. The emulsion thus formed is then cooled to ambient temperature. This emulsion remains stable for 3 months in a drying cupboard at 45° C.

EXAMPLE 20

Example of an Emulsion According to the Invention Preparation of a Cream 3 g of the emulsifying agent of Example 1 are suspended in 47 g of water obtained by osmosis. The mixture is heated to 50° C. and then stirred (at 500 rpm) for 2 minutes. The emulsion thus formed is then cooled to ambient temperature. This emulsion remains stable for 3 months in a drying cupboard at 45° C.

EXAMPLE 21

Example of a Fluid Emulsion According to the Invention 2 g of the emulsifier based on polyglycosides of Example 1 are heated with 5 g of sunflower oil and 43 g of water obtained by osmosis at the same time to a temperature of 70° C., then the mixture is homogenised (1300 rpm) at the same temperature for 1 minute and finally cooled to a temperature of the order of 25° C. with slow stirring (300 rpm). After one day of maturing, the viscosity of the emulsion thus formed is 6130 cp (BROOKFIELD DV II—25° C.—12 rpm—module 3). This emulsion remains stable for 3 months in a drying cupboard at 45° C.

EXAMPLE 22

Example of an Emulsion According to the Invention Preparation of a Cream 3 g of the emulsifier based on polyglycosides of Example 7 are heated with 15 g of isostearyl isostearate and 32 g of water obtained by osmosis at the same time to a temperature of 70° C., then the mixture is homogenised (1300 rpm) at the same temperature for 1 minute and finally cooled to a temperature of the order of 25° C. with slow stirring (300 rpm). After one day of maturing, the viscosity of the emulsion thus formed is 20000–25000 cp (BROOKFIELD DV II—25° C.—12 rpm—module 3). This emulsion remains stable for 3 months in a drying cupboard at 45° C.

EXAMPLE 23

Example of a Fluid Emulsion According to the Invention

The lipophilic phase (10 g of isostearyl isostearate) which contains 4 g of emulsifier based on polyglycosides according to Example 7 and the hydrophilic phase (86 g of water obtained by osmosis) are heated separately to a temperature of 70° C. The lipophilic phase is vigorously agitated (800 rpm) and within 2 minutes the hydrophilic phase is added until phase inversion occurs characterised by an abrupt change in viscosity. From then on it may be added more rapidly (1 minute). The emulsion is then left to cool with gentle stirring (300 rpm) to a temperature of the order of 25° C.

After 1 day of maturing, the viscosity of the emulsion thus formed is 6960 cp (BROOKFIELD DV II—25° C.—12 rpm—module 3). This emulsion remains stable for 3 months in a drying cupboard at 45° C.

EXAMPLE 24

Example of an Emulsion According to the Invention Preparation of a Cream

The lipophilic phase (10 g of miglyol) which contains 4 g of emulsifier based on polyglycosides according to Example 8 and the hydrophilic phase (86 g of water obtained by osmosis) are heated separately to a temperature of 70° C. The lipophilic phase is vigorously agitated (800 rpm) and within 2 minutes the hydrophilic phase is added until phase inversion occurs characterised by an abrupt change in viscosity. From then on it may be added more rapidly (1 minute). The emulsion is then left to cool with gentle stirring (300 rpm) to a temperature of the order of 25° C.

After 1 day of maturing, the viscosity of the emulsion thus formed is 11320 cp (BROOKFIELD DV II—25° C.—12 rpm—module 3). This emulsion remains stable for 3 months in a drying cupboard at 45° C.

EXAMPLE 25

Example of a Fluid Emulsion According to the Invention

The lipophilic phase (10 g of a mixture of sunflower oil: 50% and dimethicone: 50%) which contains 4 g of emulsifier based on polyglycosides according to Example 11 and the hydrophilic phase (86 g of water obtained by osmosis) are heated separately to a temperature of 70° C. The lipophilic phase is vigorously agitated (800 rpm) and within 2 minutes the hydrophilic phase is added until phase inversion occurs characterised by an abrupt change in viscosity. From then on it may be added more rapidly (1 minute). The emulsion is then left to cool with gentle stirring (300 rpm) to a temperature of the order of 25° C.

This emulsion remains stable for 3 months in a drying cupboard at 45° C.

EXAMPLE 26

Example of a Fluid Emulsion According to the Invention

The lipophilic phase (10 g of isostearyl isostearate) which contains 4 g of,emulsifier based on polyglycosides according to Example 1 and the hydrophilic phase (86 g of water obtained by osmosis) are heated separately to a temperature of 70° C. The lipophilic phase is agitated (1500 rpm) and the lipophilic phase is progressively added thereto. The emulsion is then left to cool with gentle stirring (300 rpm) to a temperature of the order of 25° C.

After 1 day of maturing, the viscosity of the emulsion thus formed is 6130 cp (BROOKFIELD DV II—25° C.—12 rpm—module 3). This emulsion remains stable for 3 months in a drying cupboard at 45° C.

EXAMPLE 27

Example of an Emulsion According to the Invention Preparation of a Cream 30 g of the emulsifier based on polyglycosides of Example 3, 100 g of isostearyl isostearate and 870 g of water obtained by osmosis are heated simultaneously to a temperature of 70° C. and then homogenised (150 rpm) at the same temperature for 1 minute. The mixture is left to cool to 50°C. and the medium is placed in a high-pressure homogeniser (300 bar). After 1 day maturing, the viscosity of the emulsion thus formed is 6160 cp (BROOKFIELD DV II—25° C.—12 rpm—module 3).

EXAMPLE 28

Example of a Concentrated Emulsion for Plant Protection According to the Invention 2

2 g of the emulsifier based on polyglycosides according to EXAMPLE 15, 70 g of rape seed oil and 28 g of water obtained by osmosis are heated at the same time to a temperature of 75° C. and then homogenised (10000 rpm) at the same temperature for 2 minutes and finally cooled with gentle stirring (300 rpm) to a temperature of the order of 25° C. After 1 day maturing, the viscosity of the emulsion thus formed is 1060 cp (BROOKFIELD DV II—25° C.—12 rpm—module 3). This emulsion remains stable for 2 months in a drying cupboard at 45° C.

EXAMPLE 29

Example of a Concentrated Emulsion for Plant Protection According to the Invention 2 g of the emulsifier based on polyglycosides according to Example 16, 70 g of rape seed ester (Robbe ester) and 28 g of water obtained by osmosis are heated at the same time to a temperature of 75° C. and then homogenised (10000 rpm) at the same temperature for 2 minutes and finally cooled with gentle stirring (300 rpm) to a temperature of the order of 25° C. After 1 day maturing, the viscosity of the emulsion thus formed is 1800 cp (BROOKFIELD DV II—25° C.—12 rpm—module 3). This emulsion remains stable for 2 months in a drying cupboard at 45° C.

EXAMPLE 30

Example of a Dilute Emulsion for Plant Protection According to the Invention 0.5 g of the emulsion of Example 28 and 19.5 g of water are placed in a tube, then they are mixed by turning the tube over three times in succession. The emulsion obtained is stable for 2 hours, corresponding to the time needed for the farmer to use the product, for example.

EXAMPLE 31

Example of a Gas Oil Emulsion According to the Invention 1 g of the emulsifier based on polyglycosides according to Example 15, 69.5 g of gas oil and 29.5 g of water obtained by osmosis are heated simultaneously to a temperature of 65° C. and then homogenised (9500 rpm) at the same temperature for 2 minutes and finally cooled with gentle stirring (300 rpm) to a temperature of the order of 25° C.

COMPARATIVE EXAMPLE 32

Foaming Indices of the Emulsions Prepared from the Emulsifiers Based on Polyglycosides and Fatty Alcohols According to the Invention Preparation of the Emulsions Compositions:

3% by weight, based on the total weight of the emulsion, of emulsifier based on polyglycosides and fatty alcohols 10% by weight, based on the total weight of the emulsion, of sunflower oil 0.5% by weight, based on the total weight of the emulsion, of preservative (Phenonip®)

water obtained by osmosis qs ad 100% by weight.

Method:

The ingredients are weighed successively in a short beaker and heated for 10 minutes to 75° C. The medium is stirred for 1 minute at 15,000 rpm using a polytron. Stirring is continued with a bar magnet (200 rpm) for 30 minutes until the emulsion has cooled. The emulsion is left to stand for 24 hours at 25° C. before being analysed.

All the emulsifiers based on polyglycosides and fatty alcohols used contain 55% by weight, based on the total weight of the compositions, of a mixture of hexadecanol and octadecanol (50/50 weight/weight). The polyglycosides consist of polyhexosides (polyglucosides of synthesis Example 3) and/or polypentosides (polyxylosides of Example 17).

Foaming Index

The foaming index is defined as the percentage by volume of residual emulsion after a treatment of destabilisation by centrifuging. The centrifugations (4080 g for 1 hour) are identical for all the tests. After centrifuging, the foaming index is the ratio of the volume of residual emulsion over the total volume of initial emulsion multiplied by 100.

The results are summarised in the following Table:

| CONSTITUTION OF THE EMULSIFIER BASED ON POLYGLYCOSIDES | | |
| --- | --- | --- |
| Polyglucosides of synthesis Example 3 (%/total polyglycoside) | Polyxylosides of Example 17 (%/total polyglycosides) | Foaming index |
| 100 | 0 | 19.5% |
| 34 | 66 | 98.5% |
| 30 | 70 | 99.5% |
| 20 | 80 | 99.7% |
| 10 | 90 | 99.7% |
| 0 | 100 | 100% |

The above Table demonstrates that the emulsifiers based on polyglycosides containing 66% to 100% by weight, based on the total weight of the polyglycosides, polypentosides and 0 to 34% by weight of polyhexosides, result in emulsions having a foaming index of nearly 100%, i.e. which are stable when centrifuged; this is not the case for compositions containing exclusively polyhexosides, such as the polyglucosides of synthesis Example 3.

EXAMPLE 33

Process for Preparing a Comparative Emulsifier

In order to demonstrate the particular properties of the emulsifiers according to the present invention, we prepared the following comparative emulsifier: 65 g of the emulsifier based on polyglucoside in synthesis Example 1 and 35 g of the emulsifier based on polyxyloside of Example 1 are mixed to obtain 100 g of emulsifier based on polyglycosides containing 35% by weight, based on the polyglycosides, of polypentosides (polyxylosides) and 65% by weight of polyhexosides (polyglucosides).

COMPARATIVE EXAMPLE 34

Variation in the Retrodiffusion of Emulsions Prepared From the Emulsifiers Based on Polyglycosides and Fatty Fatty Alcohols According to the Invention Principle of the Analysis The method of analysis used to evaluate the relative stabilities of the emulsions is based on measuring the retrodiffusion of the emulsion using a TURBISCAN. This instrument for macroscopic analysis with vertical scanning uses an infra-red close-up detector. This carries our full optical scanning over the entire height of the sample of emulsion and gives the macroscopic appearance of the emulsion at a given time in the form of a graph or tables. Designed to operate kinetically, it detects the physical developments in the emulsion by simply comparing graphic profiles. This technique enables it to detect phenomena of foaming, clarification, sedimentation and coalescence which are synonymous with the destabilisation of the emulsions long before they are visible to the naked eye. The most stable emulsions are those which have the least variation in retrodiffusion as a function of time.

Preparation of the Emulsions

Compositions:

2% by weight of emulsifier, based on the total weight of the emulsion

30% by weight of sunflower oil, based on the total weight of the emulsion 0.4% by weight of preservative (Phenonip®) based on the total weight of the emulsion water obtained by osmosis qs ad 100% by weight.

Method:

The ingredients are weighed successively in a tall beaker and heated for 10 minutes to 75° C. The medium is agitated for 1 minute at 15,000 rpm using a polytron. Agitation is continued using a bar magnet (200 rpm) for 30 minutes until the emulsion has cooled. The analyses are carried out immediately after the preparation of the emulsions.

All the emulsifiers based on polyglycosides and fatty alcohols used contain 50% by weight, based on the total weight of the compositions, of a mixture of tetradecanol and octadecanol (25/75 weight/weight). The emulsions compared are as follows:

| Emulsion No. | 1 | 2 | 3 | 4 |
|---|---|---|---|---|
| Emulsifier according to the invention | Example 1 | Example 11 | — | — |
| Comparative emulsifier | — | — | Example 33 | Synthesis Example 1 |
| % of polypentosides/ polyglycosides in the emulsifier | 100% | 90% | 35% | 0% |
| % of polyhexosides/ polyglycosides in the emulsifier | 0% | 10% | 65% | 100% |

The results are summarised in the following Table:

Variation in retrodiffusion as a function of time measured in the bottom of the tubes containing the emulsions to be analysed

| Emulsion No. | Time in hours | | | |
|---|---|---|---|---|
| | 5 | 10 | 20 | 27 |
| 1 | 2.5% | 3.5% | 5.5% | 7% |
| 2 | 4.5% | 7% | 10% | 12.5% |
| 3 | 9% | 13.5% | 17% | 20% |
| 4 | 13% | 25% | 26% | 28% |

The above Table shows that the emulsions prepared from the emulsifiers according to the invention (nos. 1 and 2) have smaller variations in retrodiffusion as a function of time than those observed with the emulsions prepared from the comparative emulsifiers (nos. 3 and 4). The emulsions according to the present invention are therefore more stable.

COMPARATIVE EXAMPLE 35

Variation in the Retrodiffusion of Emulsions Prepared From the Emulsifiers Based on Polyglycosides and Fatty Alcohols According to the Invention This comparative Example is carried out in the same way as the preceding comparative Example 34 except that the sunflower oil is replaced by Miglyol 812 N marketed by Lambert Riviere.

The emulsions compared are as follows

| Emulsion No. | 5 | 6 | 7 | 8 |
|---|---|---|---|---|
| Emulsifier according to the invention | Example 1 | Example 11 | — | — |
| Comparative emulsifier | — | — | Example 33 | Synthesis Example 1 |
| % of polypentosides/ polyglycosides in the emulsifier | 100% | 90% | 35% | 0% |
| % of polyhexosides/ polyglycosides in the emulsifier | 0% | 10% | 65% | 100% |

The results are summarised in the following Table:

Variation in retrodiffusion as a function of time measured in the bottom of the tubes containing the emulsions to be analysed

| Emulsion No. | Time in hours | | | |
|---|---|---|---|---|
| | 5 | 10 | 15 | 20 |
| 5 | 3.5% | 3.5% | 3.5% | 3.5% |
| 6 | 4% | 5% | 6.5% | 8% |
| 7 | 21% | 27% | 27.5% | 28.5% |
| 8 | 16% | 24.5% | 25% | 26% |

Percentage of residual emulsion measured as a function of time by analysing the retrodiffusion over the entire height of the tubes containing the emulsions

| Emulsion No. | Time in hours | | | |
|---|---|---|---|---|
| | 5 | 10 | 15 | 20 |
| 5 | 99% | 99% | 99% | 99% |
| 6 | 98% | 97% | 95% | 93% |
| 7 | 86% | 77% | 76% | 75% |
| 8 | 93% | 85% | 83% | 81% |

The preceding Tables show on the one hand that the emulsions prepared from the emulsifiers according to the invention (Nos. 5 and 6) have smaller variations in retrodiffusion as a function of time than those observed with the emulsions prepared from the comparative emulsifiers (Nos. 7 and 8). Moreover, the residual emulsions obtained with the emulsifiers according to the invention (Nos. 5 and 6) are broadly superior to those obtained with the comparative agents (Nos. 7 and 8). The emulsions according to the present invention are thus more stable.

COMPARATIVE EXAMPLE 36

Foaming Indices of the Emulsions Prepared from the Emulsifiers Based on Polyglycosides and Fatty Alcohols According to the Invention Preparation of Emulsions
  Compositions:
  2% by weight, based on the total weight of the emulsion, of emulsifier based on polyglycosides and fatty alcohols
  30% by weight of oil, based on the total weight of the emulsion
  0.4% by weight of preservative (Phenonip®), based on the total weight of the emulsion
  water obtained by osmosis qs ad 100% by weight.
  Method:
  The ingredients are weighed successively in a short beaker and heated for 10 minutes to 75° C. The medium is agitated for 1 minute at 15,000 rpm using a polytron. Stirring is continued with a bar magnet (200 rpm) for 30 minutes until the emulsion has cooled. The emulsion is left to stand for 24 hours at 25° C. before being analysed.
  All the emulsifiers based on polyglycosides and fatty alcohols used contain 50% by weight, based on the total weight of the compositions, of a mixture of tetradecanol and octadecanol (25/75 weight/weight).
Foaming Index
  The foaming index is defined as the percentage by volume of residual emulsion after a treatment of destabilisation by centrifuging. The centrifugations (4080 g for 1 hour) are identical for all the tests. After centrifuging, the foaming index is the ratio of the volume of residual emulsion over the total volume of initial emulsion multiplied by 100.
  The emulsions were prepared with two different oils, Miglyol 812N marketed by Lambert Rivière and isostearyl isostearate marketed by Gattefossé. The emulsions compared are as follows: With Miglyol 812N:

| Emulsion No. | 9 | 10 | 11 | 12 |
|---|---|---|---|---|
| Emulsifier according to the invention | Example 1 | Example 11 | — | — |
| Comparative emulsifier | — | — | Example 33 | Synthesis Example 1 |
| % of polypentosides/polyglycosides in the emulsifier | 100% | 90% | 35% | 0% |
| % of polyhexosides/polyglycosides in the emulsifier | 0% | 10% | 65% | 100% |

With isostearyl isostearate:

| Emulsion No. | 13 | 14 | 15 | 16 |
|---|---|---|---|---|
| Emulsifier according to the invention | Example 1 | Example 11 | — | — |
| Comparative emulsifier | — | — | Example 33 | Synthesis Example 1 |
| % of polypentosides/polyglycosides in the emulsifier | 100% | 90% | 35% | 0% |
| % of polyhexosides/polyglycosides in the emulsifier | 0% | 10% | 65% | 100% |

The results are summarised in the Table which follows:

| Emulsion No. | Foaming index (%) |
|---|---|
| 9 | 100 |
| 10 | 100 |
| 11 | 58 |
| 12 | 58 |
| 13 | 100 |
| 14 | 100 |
| 15 | 66 |
| 16 | 77 |

The above Table shows that the emulsifiers according to the invention (Nos. 9, 10, 13 and 14) make it possible to form emulsions having a foaming index of approximately 100%, i.e. they are estable on centrifuging; this is not the.case with the emulsions prepared from the comparative emulsifiers (Nos. 11, 12, 15 and 16).

EXAMPLE 37

Measuring the Long Term Stability of the Emulsions According to the Present Invention by Analysing Their Retrodiffusion Principle of Analysis
  The principle of analysis is identical to that described in comparative Example 34.
Preparation of the Emulsions
  Compositions:
  4% by weight, based on the total weight of the emulsion, of emulsifier according to Example 7
  30% by weight of sunflower oil, based on the total weight of the emulsion
  0.4% by weight of preservative (Phenonip®) based on the total weight of the emulsion
  water obtained by osmosis qs ad 100% by weight.
  Method:
  The ingredients are weighed successively in a tall beaker and heated for 10 minutes to 75° C. The medium is stirred for 1 minute at 1300 rpm. Stirring is continued with a bar magnet (200 rpm) for 30 minutes until the emulsion cools. After one day standing at 25° C. the emulsion is placed in a drying chamber at 40° C. and analysed regularly using a retrodiffusion analyser (Turbiscan).

The results are summarised in the following Table:

Percentage of residual emulsion determined by analysing retrodiffusion as a function of time

| Time (Days) | % of residual emulsion |
|---|---|
| 0 | 100 |
| 10 | 100 |
| 30 | 100 |
| 50 | 100 |
| 70 | 100 |

The above Table shows that the emulsion is perfectly stable over time after being stored at 40° C.

COMPARATIVE EXAMPLE 38

Suspending Power of the Emulsions Prepared From the Emulsifiers Based on Polyglycosides and Fatty Alcohols According to the Invention Principle In order to evaluate the suspending powers of the emulsions according to the present invention, we prepared them and added, as additives, solid particles ranging in size between 0.05 and 0.250 mm. We then subjected the emulsions to a destabilising treatment by centrifuging at 2000 rpm for 3 minutes at 2021° C. We then measured the residue of solid particles deposited at the base of the tube. The results are expressed as a percentage of residue defined by the volume of residue in relation to the total volume of emulsion centrifuged. The emulsions with the best suspending powers are those for which we had no residue at all.

Preparation of the Emulsions

Compositions:

3% by weight, based on the total weight of the emulsion, of emulsifier based on polyglycosides and fatty alcohols 10% by weight, based on the total weight of the emulsion, of oil (isostearyl isostearate)

5% by weight of solid particles ranging from 0.05 to 0.25 mm in diameter 0.5% by weight, based on the total weight of the emulsion, of preservative (Phenonip®)

water obtained by osmosis qs ad 100% by weight.

Method:

The ingredients are weighed successively in a low beaker and heated for 10 minutes to 75° C. The medium is stirred for 1 minute at 1300 rpm. Stirring is continued with a bar magnet (200 rpm) for 30 minutes until the emulsion has cooled. The emulsion is left to stand for 24 hours at 25° C. before being analysed.

The emulsifiers based on polyglycosides and fatty alcohols used contain 50% by weight, based on the total weight of the compositions, of a mixture of hexadecanol and octadecanol (33/67; weight/weight). The polyglycosides consist of polyhexosides (polyglucosides of synthesis Example 2) or polypentosides (polyxylosides of Example 2).

The results are summarised in the following Table:

| EMULSIFIER | SUSPENDING POWER |
|---|---|
| Comparative emulsifier from synthesis Example 2 | 12% |
| Emulsifier from Example 2 according to the invention | 0% |

The above Table shows that the emulsifier of Example 2 according to the invention makes it possible to form emulsions having excellent suspending power, i.e. free from any residue obtained after centrifugation; this is not the case with the comparative emulsifier of synthesis Example 2 for which the emulsions leave a deposit of 12%.

EXAMPLE 39

| | Water-resistant self-tanning and moisturising cream | |
|---|---|---|
| A | Emulsifier of Example 4 | 4.0% |
| | Aloe vera | 1.0% |
| | Shea tree butter | 0.2% |
| | Dimethicone | 2.0% |
| | 2-octyl dodecyl myristate (MOD) | 3.0% |
| | Propylglycol stearate (Stepan PGMS) | 1.0% |
| | Stearic acid | 1.0% |
| | Vitamin E | 0.1% |
| | Hyaluronic acid (VITALHYAL) | 1.0% |
| | Phenonip | 0.5% |
| B | Glycerol | 10% |
| | Water | qs ad 100% |
| C | Dihydroxyacetone | 5.0% |
| | Water | 10.0% |
| D | Fragrance | QS |

Process for producing the cream:

All the ingredients of A are weighed

All the ingredients of B are weighed and homogenised

They are separately heated to 75° C.

A is stirred at 800 rpm

B is added to A in a stream

They are mixed together at 1300 rpm for some minutes at 75° C.

The mixture is left to cool to 40° C. while stirring at 300 rpm

Solution C is prepared at ambient temperature C and D are added to the emulsion

The pH is corrected if necessary.

EXAMPLE 40

| Moisturising lotion | |
|---|---|
| Emulsifier of Example 10 | 2.0% |
| Miglyol 812 N | 3.0% |
| Isostearyl isostearate | 3.0% |
| Dimethicone | 2.0% |
| Stearic acid | 1.0% |
| Hyaluronic acid (VITALHYAL) | 1.0% |
| Phenonip | 0.5% |
| Water | qs ad 100% |

Process for preparing the lotion:

All the ingredients are weighed
They are heated to 75° C.
They are mixed at 3000 rpm for some minutes at 75° C.
They are left to cool at 30° C. whilst stirring at 500 rpm
The pH is corrected if necessary.

| Makeup removing lotion | | | |
|---|---|---|---|
| A | Emulsifier of Example 7 | 4.0% | |
| | Shea tree butter | 2.0% | |
| | Dimethicone | 2.0% | |
| | Sweet almond oil | 2.0% | |
| | Jojoba oil | 3.0% | |
| | Hydrogenated cotton seed oil | 3.0% | |
| B | Vitamin E | 0.5% | |
| | Vitalhyal | 5.0% | |
| | Muciliance | 0.05% | |
| | Corn peptides | 0.5% | |
| | Solavena | 1.0% | |
| | Phenonip | 0.4% | |
| | Water | qs ad 100% | |
| C | Gel white (3% in water) | 10.0% | |
| D | Perfume | QS | |
| | Colour | QS | |

Process for preparing the lotion:

All the ingredients of A are weighed and heated to 75° C.
All the ingredients of B are weighed and heated to 75° C. with stirring
B is added to A with stirring at 800 rpm and at 75° C.
The mixture is stirred for 2 minutes at 1300 rpm
It is stirred at 200 rpm until the temperature reaches 40° C.
C is added
The pH is corrected if necessary
D is added.

| Night cream | |
|---|---|
| Emulsifier of Example 8 | 4.0% |
| Dimethicone | 2.0% |
| Jojoba oil | 1.5% |
| Sweet almond oil | 1.5% |
| MOD | 5.0% |
| Stearic acid | 2.0% |
| Corn Oil | 1.0% |
| Solavena | 1.0% |
| Vitalhyal (hyaluronic acid) | 2.0% |
| Vitamin E | 0.5% |
| Phenonip | 0.5% |
| Fragrance | QS |
| Colour | QS |
| Water | QSP 100% |

Process for producing the cream:

All the ingredients with the exception of the fragrance are weighed
They are heated to 75° C.
They are then mixed at 300 rpm for some minutes until the temperature reaches 40° C.
The pH is adjusted
The fragrance is added
The mixture is placed in a homogeniser at 300 bar.

EXAMPLE 43

| Fluid wrinkle removing cream | |
|---|---|
| Emulsifier of Example 9 | 4.0% |
| Miglyol 812 N | 10.0% |
| Hyaluronic (Vitalhyal) | 2.0% |
| Exfoliator | 5.0% |
| Phenonip | 0.5% |
| Fragrance | QS |
| Water | qs ad 100% |

Process for producing the fluid cream:

All the ingredients except the fragrance are weighed
Heated to 50° C.
Mixed at 1300 rpm for some minutes
Left to cool with stirring at 300 rpm
The fragrance is added at 25° C.
The pH is corrected if necessary.

EXAMPLE 44

| Eye contour cream gel | | |
|---|---|---|
| A. | Mucic acid (Muciliance) | 0.05% |
| | Water | qs ad 100% |
| B. | Emulsifier of Example 12 | 3.0% |
| | Bashyal | 1.0% |
| | Vitalhyal | 2.0% |
| | Phenonip | 0.4% |
| C. | Cornflower water | 10.0% |

Method

The ingredients of A are mixed
The pH is adjusted to 6 with 1N sodium hydroxide
B is added to A
Heated to 75°
Stirred for 1 minute at 500 rpm
Left to cool with stirring at 300 rpm
C is added at 30° C.

EXAMPLE 45

| Nutrient balm for hair | |
|---|---|
| Emulsifier of Example 14 | 3.0% |
| Dimethicone | 1.0% |
| Corn oil | 0.5% |
| Corn peptides | 0.5% |
| Phenonip | 0.5% |
| Perfume qs | |
| Water | qs ad 100% |

Method of Preparation:

Everything except the perfume is weighed
Heated to 75° C.
Stirred at 1300 rpm for 1 minute
Cooled to 300 rpm to a temperature of 25° C.

EXAMPLE 46

| Anti-acne cream | |
| --- | --- |
| Composition of Example 13 | 4.0% |
| Paraffin Oil (MARCOL 82) | 2.0% |
| Miglyol 812 N | 3.0% |
| Isostearyl isostearate | 3.0% |
| Dimethicone | 2.0% |
| Stearic acid | 2.0% |
| Lipid sophoroses (SOPHOLIANCE) | 1.0% |
| Phenonip | 0.5% |
| Water | qs ad 100% |

Process for preparing the cream:

A clear aqueous solution of SOPHOLIANCE containing 25% dry matter is prepared, pH 6 (NaOH).

All the ingredients except SOPHOLIANCE are weighed

Heated to 75° C. for 10 minutes

Mixed at 1500 rpm for 1 minute at 75° C.

Allowed to cool with stirring at 300 rpm

SOPHOLIANCE is added at about 50° C.

The pH is corrected if necessary

Stirring is stopped at about 30° C.

What is claimed is:

1. An emulsion comprising, by weight:

4.5–99.5% of water;

0–95% of oil;

0–50% of active substance;

an emulsifier making up the total of 100% which is the only emulsifier present, wherein the emulsifier contains 30 to 65% by weight of at least one fatty alcohol of formula ROH, wherein R is straight-chained or branched aliphatic radical, which may be saturated or unsaturated, having 1 to 4 ethylenic unsaturations, having 12 to 22 carbon atoms, the emulsion further comprising (a), (b), or (c) as follows:

(a) a mixture of polyglycosides comprising polypentosides of formula (I):

$$R^1O(P)_{n1} \qquad (I)$$

wherein $R^1$ is a straight-chained or branched, saturated or unsaturated aliphatic radical having 1 to 4 ethylenic unsaturations, with 16 to 18 carbon atoms, P is the residue of a pentose selected from the group consisting of arabinose and xylose, n is between 1 and 5; said mixture of polyglycosides further comprising polyhexosides of formula (II):

$$R^2O(H)_{n2} \qquad (II)$$

wherein $R^2$ s a straight-chained or branched, saturated or unsaturated aliphatic radical having 1 to 4 ethylenic unsaturations, with 16 to 18 carbon atoms, H is the residue of a hexose, n2 is between 1 and 5;

(b) a mixture of polyglycosides of formula (III):

$$R^3O(G_1)_a(G_2)_b(G_3)_c(G_4)_d(G_5)_e \qquad (III)$$

wherein $R^3$ is a straight-chained or branched, saturated or unsaturated aliphatic radical having 1 to 4 ethylenic unsaturations, with 16 to 18 carbon atoms, $G_1$, $G_2$, $G_3$, $G_4$, and $G_5$ independently of one another are residues of a pentose, wherein said pentose is selected from the group consisting of arabinose and xylose; a, b, c, d, and e being equal to 0 or 1, the sum of a, b, c, d, and e being at least 1;

(c) or a mixture of a and b wherein;

1) when the emulsifier contains polyglycosides comprising polypentosides of formula (I) and polyhexosides of formula (II), the polypentosides of formula (I) represent 66 to 100% by weight of the total polyglycosides, and the polyhexosides of formula (II) constitute 0 to 34% by weight of the total polyglycosides, and when the emulsifier comprises polyglycosides of formula (III), the pentoses then constitute 66 to 100% by weight based on the total oses $G_1$, $G_2$, $G_3$, $G_4$, and $G_5$ and the hexoses constitute from 0 to 34% by weight based on the total oses $G_1$, $G_2$, $G_3$, $G_4$, and $G_5$ and 2-a) the emulsifier constitutes at least 2.5% of total weight of the emulsion 2-b) or the emulsifier constitutes from 1 to 2.5 % of the total weight of the emulsion and the oil is selected from the group consisting of: sweet almond oil, coconut oil, castor oil, jojoba oil, olive oil, rape seed oil, groundnut oil, hazelnut oil, palm oil, apricot kernel oil, calophyllum oil, safflower oil, avocado oil, blackcurrant seed oil, sunflower oil, corn seed oil, soya oil, cotton seed oil, alfalfa oil, barley oil, grapeseed oil, poppy oil, pumpkin oil, sesame oil, rye oil, evening primrose oil, passionflower oil, derivatives of these oils, hydrogenated oils, oils of animal origin, synthetic oils, poly-α-olefines, lanolin derivatives, alkanediols having 2 to 10 carbon atoms, alcohols of formula $R^4$—OH wherein $R^4$ is a straight-chained or branched, saturated or unsaturated aliphatic radical having 1 to 4 ethylenic unsaturations and 12 to 22 carbon atoms, polyethylene glycols, polypropylene glycols, the fatty esters of formula $R^5$—O—CO—$R^6$ wherein $R^5$ and $R^6$ independently of each other denote straight-chained or branched, saturated or unsaturated aliphatic radicals having 1 to 4 ethylenic unsaturations, with 1 to 22 carbon atoms, and the silicone oils.

2. The emulsion according to claim 1 wherein the emulsifier comprising 2.5 to 10% of the total weight of the emulsion.

3. The emulsion according to claim 1, wherein when the emulsifier comprises polyglycosides comprising polypentosides of formula (I) and polyhexosides of formula (II), the polypeniosides of formula (I) represent 80–100% by weight of the total polyglycosides, and the polyhexosides of formula (II) represent 0–20% by weight of the total polyglycosides and when the emulsifier contains polyglycosides of formula (III) the pentoses represent 80 to 100% by weight, based on the total oses $G_1$, $G_2$, $G_3$, $G_4$ and $G_5$ and the hexoses represent 0 to 20% by weight based on the total oses $G_1$, $G_2$, $G_3$, $G_4$ and $G_5$.

4. The emulsion according to claim 1 wherein the polypentosides consist of 85% polyxylosides or the pentose groups consist of at least 85% xylose groups.

5. The emulsion according to claim 1 wherein the polypentosides are polyxylosides or the pentose groups are xylose.

6. The emulsion according to claim 1 wherein the polyhexosides consist of at least 80% polyglucosides or the hexose groups consist of at least 80% glucose groups.

7. The emulsion according to claim 1 wherein the emulsifier contains polyglycosides of formulate (I), (II) or (III) wherein the radicals $R^1$ and $R^2$ or the radical $R^3$ are identical to the radical R of the fatty alcohol.

8. The emulsion according to claim 1 wherein the fatty alcohol of the emulsifier has 14 to 22 carbon atoms.

9. The emulsion according to claim 1 wherein the emulsifying composition contains 40 to 60% of fatty alcohol.

10. The emulsion according to claim 1 wherein the oily phase represents 2 to 60% by weight, based on the total weight of the emulsion.

11. A cosmetic or pharmaceutical composition comprising the emulsion of claim 1.

12. A plant-protection composition comprising the emulsion of claim 1.

13. The emulsion according to claim 1 wherein the emulsifier represents 2.5 to 6% of the total weight of the emulsion.

14. The emulsion according to claim 1 wherein the emulsifier represents 2.5 to 4% of the total weight of the emulsion.

15. The emulsion according to claim 1 wherein when the emulsifier contains polyglycosides comprising polypentosides of formula (I) and polyhexosides of formula (II), the polypentosides of formula (I) represent 97 to 100% by weight of the total polyglycosides, and the polyhexosides of formula (II) represent 0 to 3% by weight of the total polyglycosides and when the emulsifier contains polyglycosides of formula (III) the pentoses represent 97 to 100% by weight, based on the total oses $G_1$, $G_2$, $G_3$, G4 and $G_5$ and the hexoses represent 0 to 3% by weight based on the total oses $G_1$, $G_2$, $G_3$, G4 and $G_5$.

16. The emulsion according to claim 1 wherein the fatty alcohol of the emulsifier consists of a mixture of alcohols having 14 to 18 carbon atoms.

17. The emulsion according to claim 1 wherein the oily phase represents 10 to 30% by weight, based on the total weight of the emulsion.

18. An emulsion according to claim 1, wherein the emulsifier is capable of self-emulsifying.

* * * * *

UNITED STATES PATENT AND TRADEMARK OFFICE
CERTIFICATE OF CORRECTION

PATENT NO. : 6,596,779 B1  
DATED : July 22, 2003  
INVENTOR(S) : Jean-Noel Bertho et al.

It is certified that error appears in the above-identified patent and that said Letters Patent is hereby corrected as shown below:

<u>Title page,</u>
Item [75], should read

-- [75] Inventors: Jean-Noel Bertho, Pomacle (FR);
Philippe Mathaly, Reims (FR);
Régis de Baynast, Versailles (FR);
Véronique Dubois, Cosne sur Loire (FR) --

Signed and Sealed this

Fourteenth Day of October, 2003

JAMES E. ROGAN
*Director of the United States Patent and Trademark Office*